(12) United States Patent
Stinchfield et al.

(10) Patent No.: US 9,144,503 B2
(45) Date of Patent: Sep. 29, 2015

(54) EXPANDABLE SPINAL IMPLANT SYSTEM AND METHOD

(71) Applicant: Warsaw Orthopedic, Inc., Warsaw, IN (US)

(72) Inventors: Thomas Stinchfield, Memphis, TN (US); Julien J. Prevost, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 343 days.

(21) Appl. No.: 13/650,883

(22) Filed: Oct. 12, 2012

(65) Prior Publication Data

US 2014/0107787 A1    Apr. 17, 2014

(51) Int. Cl.
*A61F 2/44* (2006.01)
*A61F 2/30* (2006.01)
*A61F 2/28* (2006.01)

(52) U.S. Cl.
CPC ............ *A61F 2/442* (2013.01); *A61F 2/30744* (2013.01); *A61F 2/30965* (2013.01); *A61F 2/44* (2013.01); *A61F 2/4425* (2013.01); *A61F 2/4455* (2013.01); *A61F 2002/2817* (2013.01); *A61F 2002/2835* (2013.01); *A61F 2002/305* (2013.01); *A61F 2002/3008* (2013.01); *A61F 2002/3024* (2013.01); *A61F 2002/3055* (2013.01); *A61F 2002/30062* (2013.01); *A61F 2002/30064* (2013.01); *A61F 2002/30224* (2013.01); *A61F 2002/30225* (2013.01); *A61F 2002/30233* (2013.01); *A61F 2002/30235* (2013.01); *A61F 2002/30401* (2013.01); *A61F 2002/30418* (2013.01); *A61F 2002/30472* (2013.01); *A61F 2002/30484* (2013.01); *A61F 2002/30492* (2013.01); *A61F 2002/30495* (2013.01); *A61F 2002/30504* (2013.01); *A61F 2002/30523* (2013.01); *A61F 2002/30538* (2013.01); *A61F 2002/30579* (2013.01); *A61F 2002/30594* (2013.01); *A61F 2002/30601* (2013.01); *A61F 2002/30785* (2013.01); *A61F 2002/30836* (2013.01); *A61F 2002/30838* (2013.01); *A61F 2002/30841* (2013.01); *A61F 2002/30878* (2013.01);

(Continued)

(58) Field of Classification Search
CPC ......... A61F 2/44; A61F 2/4405; A61F 2/441; A61F 2/442; A61F 2/4425; A61F 2/4455; A61F 2/446; A61F 2/4465; A61F 2/447; A61F 2/4603; A61F 2/4611; A61F 2/4657; A61F 2/4684; A61F 2002/4627; A61F 2002/443; A61F 2002/30662; A61F 2230/0065; A61F 2002/3052; A61B 17/025; A61B 2017/0256
USPC ........................ 623/17.11–17.16; 606/90, 105
See application file for complete search history.

(56) References Cited

U.S. PATENT DOCUMENTS

| | | |
|---|---|---|
| 5,989,290 A | 11/1999 | Biedermann et al. |
| 6,015,436 A | 1/2000 | Schoenhoeffer |

(Continued)

*Primary Examiner* — Pedro Philogene

(57) ABSTRACT

A spinal implant comprises a first member defining a longitudinal axis and including a wall that defines an axial cavity and at least one lateral opening configured for disposal of an instrument. A second member is configured for disposal with the axial cavity and includes a wall having an axial surface disposed along a thickness thereof. The axial surface defines at least a portion of an axial opening and includes a plurality of gear teeth disposed therealong. The instrument is engageable with the teeth to axially translate the second member relative to the first member. Systems and methods of use are disclosed.

20 Claims, 13 Drawing Sheets

(52) U.S. Cl.
CPC .. *A61F 2002/448* (2013.01); *A61F 2002/4475* (2013.01); *A61F 2310/00017* (2013.01); *A61F 2310/00023* (2013.01); *A61F 2310/00029* (2013.01); *A61F 2310/00077* (2013.01); *A61F 2310/00179* (2013.01); *A61F 2310/00293* (2013.01); *A61F 2310/00359* (2013.01)

(56) References Cited

U.S. PATENT DOCUMENTS

| | | | |
|---|---|---|---|
| 6,176,881 B1 * | 1/2001 | Schar et al. | 623/17.11 |
| 6,193,756 B1 | 2/2001 | Studer et al. | |
| 6,524,341 B2 * | 2/2003 | Lang et al. | 623/17.15 |
| 6,866,682 B1 | 3/2005 | An et al. | |
| 6,908,485 B2 | 6/2005 | Crozet et al. | |
| 7,674,296 B2 | 3/2010 | Rhoda et al. | |
| 7,811,327 B2 | 10/2010 | Hansell et al. | |
| 8,062,366 B2 | 11/2011 | Melkent | |
| 8,083,780 B2 | 12/2011 | McClellan, III | |
| 8,152,851 B2 * | 4/2012 | Mueller et al. | 623/17.15 |
| 8,152,852 B2 | 4/2012 | Biyani | |
| 8,182,535 B2 | 5/2012 | Kraus | |
| 8,328,871 B2 * | 12/2012 | Capote et al. | 623/17.16 |
| 2008/0161926 A1 * | 7/2008 | Melkent et al. | 623/17.16 |
| 2008/0243254 A1 * | 10/2008 | Butler | 623/17.16 |
| 2009/0118765 A1 * | 5/2009 | Mueller et al. | 606/246 |
| 2010/0179594 A1 * | 7/2010 | Theofilos et al. | 606/247 |
| 2011/0178598 A1 | 7/2011 | Rhoda et al. | |
| 2011/0251692 A1 | 10/2011 | Mclaugilin et al. | |
| 2013/0053965 A1 * | 2/2013 | Metz-Stavenhagen | 623/17.16 |
| 2013/0066429 A1 * | 3/2013 | Capote et al. | 623/17.16 |
| 2013/0261748 A1 * | 10/2013 | Ashley et al. | 623/17.16 |
| 2014/0052249 A1 * | 2/2014 | Metz-Stavenhagen | 623/17.11 |

* cited by examiner

EXPANDABLE SPINAL IMPLANT SYSTEM AND METHOD

TECHNICAL FIELD

The present disclosure generally relates to medical devices for the treatment of musculoskeletal disorders, and more particularly to a surgical system that includes an expandable spinal implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. This disclosure describes an improvement over these prior art technologies.

SUMMARY

In one embodiment, in accordance with the principles of the present disclosure, a spinal implant is provided. The spinal implant comprises a first member defining a longitudinal axis and including a wall that defines an axial cavity and at least one lateral opening configured for disposal of an instrument. A second member is configured for disposal with the axial cavity and includes a wall having an axial surface disposed along a thickness thereof. The axial surface defines at least a portion of an axial opening and includes a plurality of gear teeth disposed therealong. The instrument is engageable with the teeth to axially translate the second member relative to the first member.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
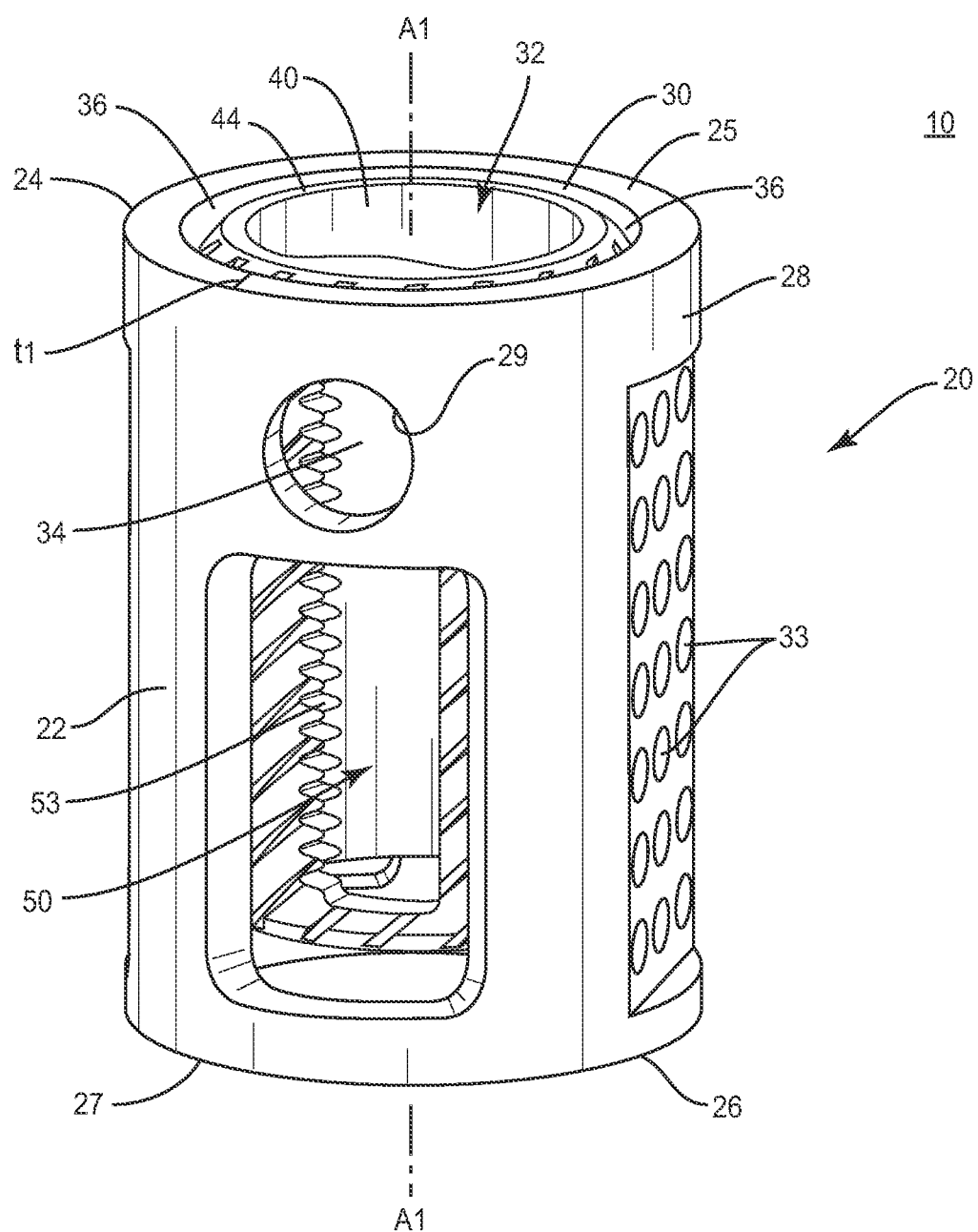
FIG. 1 is a perspective view of components of one embodiment of a surgical system in accordance with the principles of the present disclosure.
Figure 2:
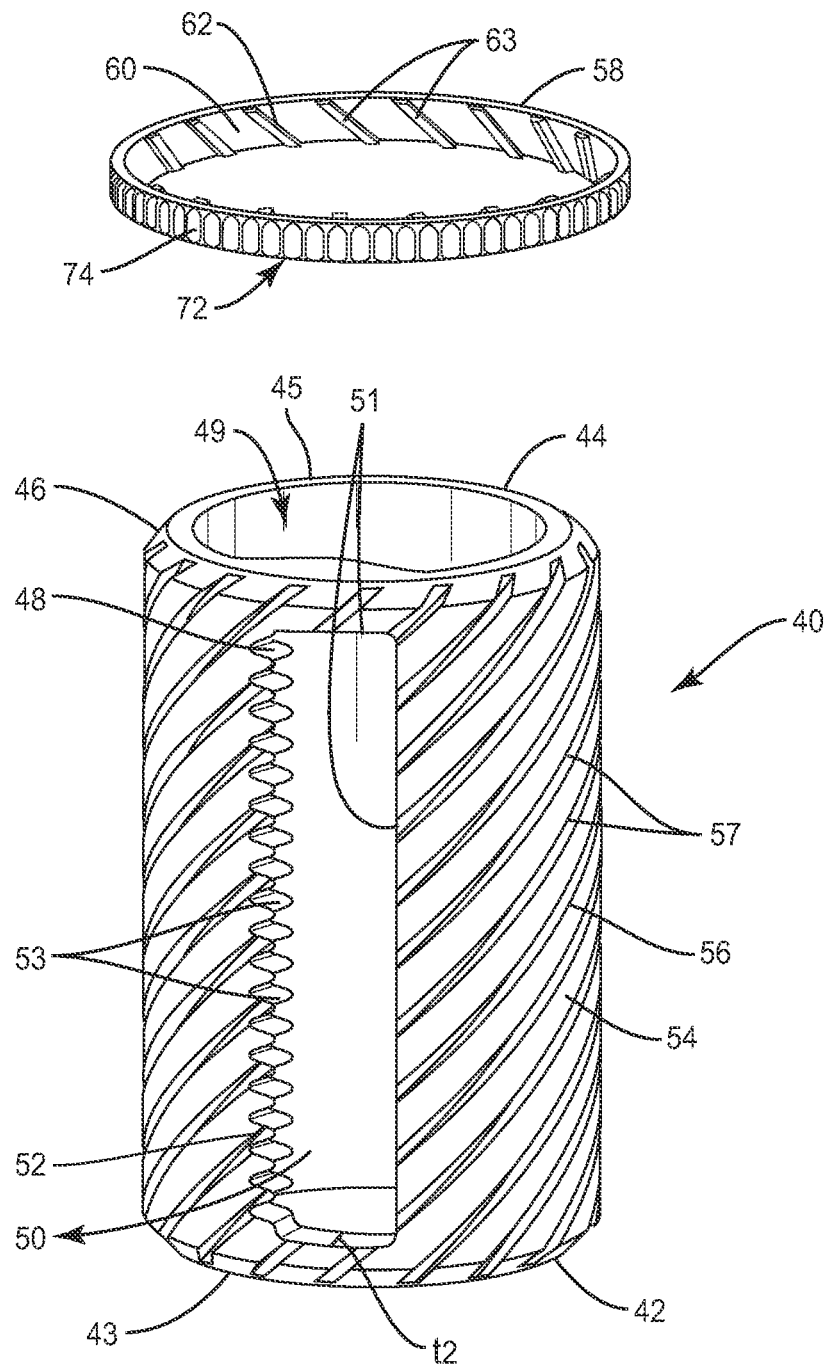
FIG. 2 is a perspective view of components of the system shown in FIG. 1 with parts separated.

The exemplary embodiments of the surgical system and related methods of use disclosed are discussed in terms of medical devices for the treatment of musculoskeletal disorders and more particularly, in terms of a surgical system that includes an expandable spinal implant and a method for treating a spine.

In one embodiment, the system includes an implant having an expansion mechanism for a continuously expandable corpectomy device. In one embodiment, the system includes an implant that is continuously expandable. In one embodiment, continuously expandable includes incremental expansion. It is envisioned that incremental expansion may include discrete increments of a particular linear dimension. It is further envisioned that the linear dimension may include a range of approximately 0.1-1.0 millimeters (mm).

In one embodiment, the system includes an implant that is expandable and employs a rack and pinion driven threaded mechanism. The threaded mechanism allows continuous expansion and is capable of a range of distraction heights. In one embodiment, the implant includes a monolithic rack. In one embodiment, the system includes an inserter instrument having a universal configuration that can be employed to adjust implants having alternate diameters and sizes.

In one embodiment, the system includes an implant having a plurality of parts. In one embodiment, the implant includes four parts. In one embodiment, the implant includes an outer body, an inner body, a ring and a locking spring. In one embodiment, the ring is inserted into a slot disposed in the inner surface of the outer body. In one embodiment, the ring is configured to rotate freely within the slot. In one embodiment, the ring includes a helical gear on its inner diameter and a spur gear on its outer diameter. In one embodiment, the helical gear is configured to mate with the inner body. It is contemplated that as the inner body expands from the outer body, the ring rotates. In one embodiment, when a desired expansion is obtained, a locking spring engages the spur gear of the ring to lock the inner body in place to prevent collapse.

In one embodiment, the inner body is expanded with a pinion shaft. In one embodiment, the pinion shaft is configured to mate with a rack disposed with the inner body. In one embodiment, as the pinion shaft is rotated, the pinion shaft drives the inner body upwards, which in turn rotates ring clockwise.

In one embodiment, the system includes an implant having a sliding lock mechanism that prevents the inner body from collapsing after the implant has expanded. It is contemplated that preventing collapse of the inner body includes resisting collapse of the inner body. In one embodiment, the sliding lock mechanism mates with a top of the outer body. In one embodiment, the lock includes teeth on its bottom surface that are configured to mate and interlock with gear teeth disposed on a top of the ring. For example, in the locked position, the interlocking teeth prevent the ring from rotating and the inner body from collapsing. For example, in the unlocked position, the lock mechanism is shifted such that the teeth are disengaged.

In one embodiment, the system includes an implant having a pin lock mechanism. In one embodiment, the pin lock includes at least one pin configured to mate with a top of the outer body. The at least one pin nests between the slots of the teeth of a spur gear disposed on the ring. The at least one pin is disengaged such that the inner body can expand or collapse. In one embodiment, the at least one pin can be adjusted depending on the axial load the implant is required to withstand. In one embodiment, to disengage the pins, the ring is turned clockwise. As the ring is turned, the surface of the slots is configured to push the pins away allowing for rotation.

In one embodiment, the system includes an implant having a locking spring. In one embodiment, to disengage the locking spring, a spring depressor is inserted through a hole in the outer body and pressed against the locking spring. As the locking spring is depressed, it forces the outer edges of the locking spring to move away from the ring to disengage from the teeth of the ring allowing for rotation. For example, to lock the implant height, the spring depressor is removed allowing the locking spring to snap back and engage the teeth of the ring.

In one embodiment, one or all of the components of the surgical system are disposable, peel-pack, pre-packed sterile devices used with an implant. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-5, there is illustrated components of a surgical system, such as, for example, a spinal implant system 10 in accordance with the principles of the present disclosure.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elastoplastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. It is contemplated that system 10 may be employed with surgical procedures, such as, for example, corpectomy and discectomy, which include fusion and/or fixation treatments that employ implants, in accordance with the principles of the present disclosure, to restore the mechanical support function of vertebrae.

System 10 includes an implant 20 having a first member, such as, for example, an outer body 22 having a tubular configuration. Body 22 extends in a linear configuration and defines a longitudinal axis A1. It is envisioned that body 22 may extend in alternate configurations, such as, for example, arcuate, offset, staggered and/or angled portions, which may include acute, perpendicular and obtuse.

Body 22 extends between a first end 24 and a second end 26. End 24 defines an end face 25 including a substantially planar surface that is configured to engage vertebral tissue. End 26 defines an end face 27 including a substantially planar surface that is configured to engage vertebral tissue. It is contemplated that end 24 and/or end 26 can include a surface that may be rough, textured, porous, semi-porous, dimpled and/or polished such that it facilitates engagement with tissue. It is further contemplated that the vertebral tissue may include intervertebral tissue, endplate surfaces and/or cortical bone. It is envisioned that both or only one of ends 24, 26 may engage tissue to provide treatment and according to the requirements of a particular surgical procedure.

Body 22 includes a wall, such as, for example, a tubular wall 28 that defines a substantially average thickness t1. It is envisioned that thickness t1 may be uniform or have alternate dimensions along the length of wall 28, for example, portions having a greater or lesser thickness. Wall 28 includes an inner surface 30 that defines an axial cavity 32 extending between ends 24, 26. It is contemplated that wall 28 has a cylindrical cross-section. It is envisioned that the cross-section geometry of wall 28 may have various configurations, such as, for example, round, oval, oblong, triangular, polygonal having planar or arcuate side portions, irregular, uniform, non-uniform, consistent, variable, horseshoe shape, U-shape or kidney bean shape. It is contemplated that surface 30 is smooth or even. It is envisioned that surface 30 may be rough, textured, porous, semi-porous, dimpled and/or polished.

Wall 28 includes an inwardly oriented surface 29 that defines a lateral opening 34. Opening 34 is configured for disposal of an instrument utilized to facilitate expansion of body 22 and a second member, such as, for example, an inner body 40 of implant 20, as described herein. Opening 34 has a circular aperture configuration and is oriented for disposal of an instrument, such as, for example, a pinion gear shaft I configured for engagement with gear teeth of body 40. Opening 34 is oriented substantially perpendicular to axis A1. It is contemplated that opening 34 may be variously oriented relative to axis A1, such as, for example, transverse and/or angled, which may include acute and obtuse orientations. It is contemplated that wall 28 may include one or a plurality of openings. It is envisioned that opening 34 may be variously configured, such as, for example, oval, oblong, triangular, polygonal having planar or arcuate side portions, irregular, uniform, non-uniform, consistent, variable, horseshoe shape, U-shape or kidney bean shape.

Figure 3:
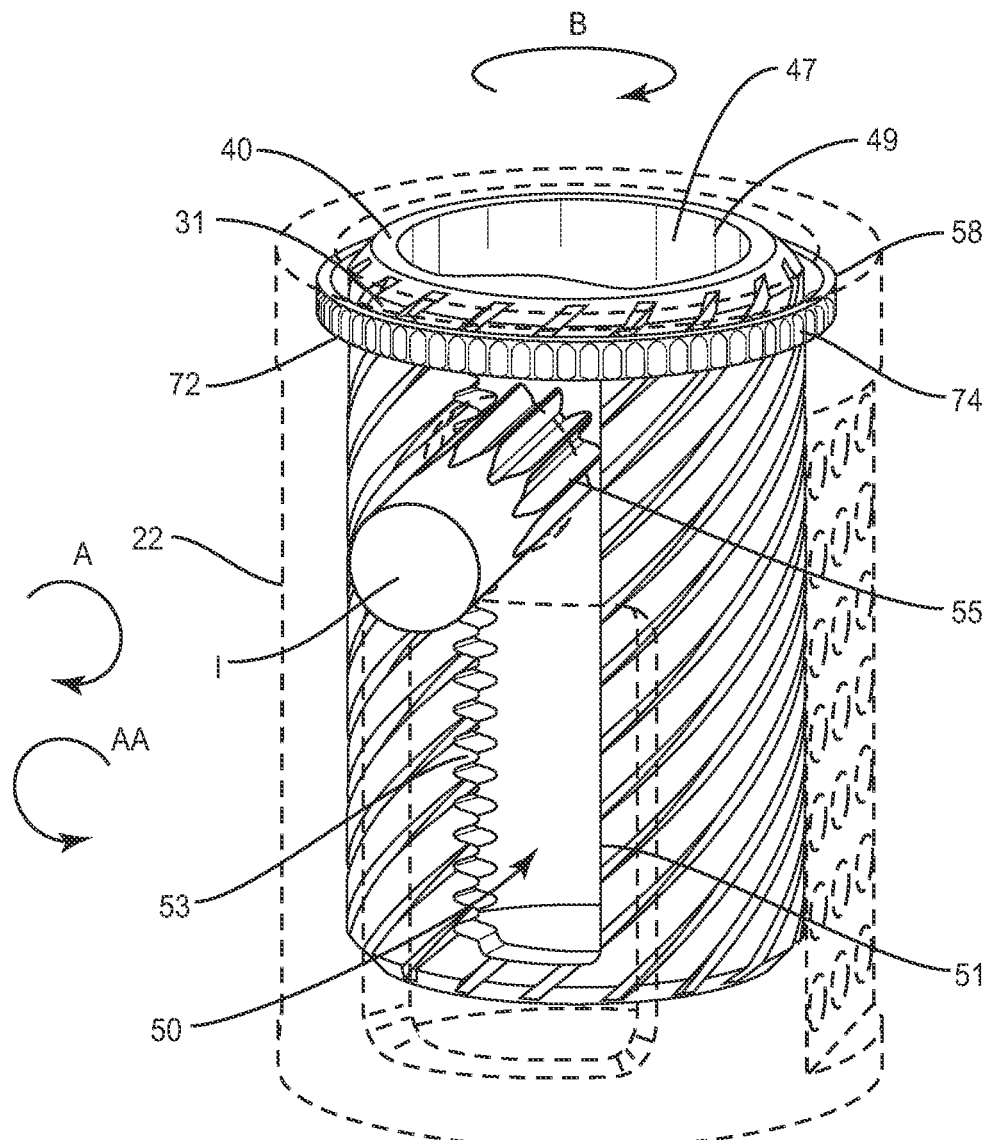
FIG. 3 is a perspective view, in part phantom, of components of the system shown in FIG. 1.

Surface 30 includes a portion 31, as shown in FIG. 3, which defines a circumferential cavity 36 disposed adjacent end 24. Portion 31 has a substantially smooth or even surface configuration such that cavity 36 is configured for disposal of a third member, such as, for example, a band 58 of implant 20. Band 58 is slidably movable within cavity 36 for rotation relative to portion 31. It is envisioned that portion 31 may be rough, textured, porous, semi-porous, dimpled and/or polished.

Wall 28 defines openings 33 configured to receive an agent, which may include bone graft (not shown) and/or other materials, as described herein, for employment in a fixation or fusion treatment used for example, in connection with a corpectomy. It is contemplated that body 22 may define one or a plurality of openings 33. Openings 33 are configured to facilitate the flow of an agent between cavity 32 and exterior to body 22 and adjacent vertebrae, as will be discussed, to promote bone growth, joint immobilization, therapy and/or treatment. It is envisioned that openings 33 can be oriented and facing a disc space and/or vertebrae. Openings 33 are oriented substantially perpendicular to axis A1. It is contemplated that one or a plurality of openings 33 may be variously oriented relative to axis A1, such as, for example, transverse and/or angled, which may include acute and obtuse orientations.

In one embodiment, the agent may include therapeutic polynucleotides or polypeptides and bone growth promoting material, which can be packed or otherwise disposed on or about the surfaces of the components of system 10, including implant 20. The agent may also include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, biologically active agents coated onto the exterior of implant 20 and/or applied thereto for gradual release such as by blending in a bioresorbable polymer that releases the biologically active agent or agents in an appropriate time dependent fashion as the polymer degrades within the patient. Suitable biologically active agents include, for example, bone morphogenic protein (BMP) and cytokines.

In one embodiment, cavity 32 may be configured as a reservoir configured as a drug depot with medication for pain and may include antibiotics and/or therapeutics. It is envisioned that cavity 32 includes active agents and may include one or a plurality of therapeutic agents and/or pharmacological agents for release, including sustained release, to treat, for example, pain, inflammation and degeneration. The agent may include pharmacological agents, such as, for example, antibiotics, anti-inflammatory drugs including but not limited to steroids, anti-viral and anti-retroviral compounds, therapeutic proteins or peptides, therapeutic nucleic acids and combinations thereof.

Body 40 has a tubular configuration and is oriented for disposal within axial cavity 32. Body 40 extends in a linear configuration relative to axis A1. It is envisioned that body 40 may extend in alternate configurations, such as, for example, arcuate, offset, staggered and/or angled portions, which may include acute, perpendicular and obtuse.

Body 40 extends between a first end 42 and a second end 44. End 42 defines an end face 43 including a substantially planar surface that is configured to engage vertebral tissue. End 44 defines an end face 45 including a substantially planar surface that is configured to engage vertebral tissue. It is contemplated that end 42 and/or end 44 can include a surface that may be rough, textured, porous, semi-porous, dimpled and/or polished such that it facilitates engagement with tissue. It is envisioned that both or only one of ends 42, 44 may engage tissue to provide treatment and according to the requirements of a particular surgical procedure.

Body 40 includes a wall, such as, for example, a tubular wall 46 that defines a substantially average thickness t2. It is envisioned that thickness t2 may be uniform or have alternate dimensions along the length of wall 46, for example, portions having a greater or lesser thickness. Wall 46 includes an inner surface 47 that defines an axial cavity 49 extending between ends 42, 44. It is contemplated that wall 46 has a cylindrical cross-section. It is envisioned that the cross-sectional geometry of wall 46 may have various configurations, such as, for example, round, oval, oblong, triangular, polygonal having planar or arcuate side portions, irregular, uniform, non-uniform, consistent, variable, horseshoe shape, U-shape or kidney bean shape. It is contemplated that surface 47 is smooth or even. It is envisioned that surface 47 may be rough, textured, porous, semi-porous, dimpled and/or polished. Body 40 is configured for disposal with cavity 32 such that walls 28, 46 are concentric with axis A1.

Wall 46 includes a plurality of inwardly oriented surfaces, which include an axial surface 48 and side surfaces 51 disposed along thickness t2. Surfaces 51 are substantially planar and smooth or even. It is envisioned that surfaces 51 may be rough, textured, porous, semi-porous, dimpled and/or polished. Surfaces 48, 51 are each disposed in a relatively perpendicular orientation to each other to define an axial opening, such as, for example, an axial slot 50. Slot 50 has a substantially rectangular configuration to facilitate axial translation and rotation of shaft I relative to body 40. It is envisioned that surfaces 48, 51 may be disposed in alternate relative orientations, such as acute or obtuse angular orientations. It is envisioned that slot 50 may have various configurations, such as, for example, round, oval, oblong, triangular, polygonal having planar or arcuate side portions, irregular, uniform or non-uniform.

Surface 48 includes a gear rack 52 having a plurality of teeth 53 that are disposed therealong. Teeth 53 are disposed in a linear, serial configuration along surface 48 and extend into a cavity defined by slot 50. Shaft I is disposed within slot 50 for relative axial translation and rotation such that circumferentially disposed gear teeth 55 of shaft I engage teeth 53. As shaft I is rotated, teeth 55 engage teeth 53 to drive body 40 in an axial direction and cause axial translation of body 40 relative to body 22 to expand implant 20, as described herein.

Body 40 includes an outer surface 54, which is circumferentially disposed thereabout. Surface 54 comprises a helical gear 56 having a plurality of teeth 57 engageable with band 58 to facilitate expansion of implant 20, as described herein. Teeth 57 are spaced apart in a helical configuration and disposed at an angular orientation relative to axis A1 such that body 40 and band 58 are rotatable relative to each other in a helical gear configuration. It is envisioned that surface 54 may be rough, textured, porous, semi-porous, dimpled and/or polished.

Band 58 has a circumferential ring configuration and is configured for disposal within cavity 36. Band 58 includes an inner surface 60, which is circumferentially disposed thereabout. Surface 60 comprises a helical gear 62 having a plurality of teeth 63 engageable with teeth 57 of gear 56. Teeth 63 are spaced apart in a helical configuration and disposed at an angular orientation relative to axis A1 such that band 58 is rotatable in a helical gear configuration. It is envisioned that surface 60 may be rough, textured, porous, semi-porous, dimpled and/or polished.

Band 58 includes an outer surface 70, which is circumferentially disposed thereabout. Outer surface 70 includes a spur gear 72 having a plurality of axially oriented and spaced apart teeth 74 configured to engage a lock to prevent axial translation of body 40 relative to body 22, as described herein. As band 58 rotates within cavity 36, teeth 74 rotate relative to portion 31. In one embodiment, teeth 74 slidably engage portion 31.

As shaft I is rotated, body 40 is driven in an axial direction and body 40 axially translates relative to body 22 such that gear 56 engages gear 62. As gears 56, 62 engage, band 58 slidably rotates within cavity 36 for rotation relative to portion 31 in a configuration to facilitate expansion of implant 20. Body 40 axially translates relative to body 22 and band 58 is disposed therewith between a first, contracted or nested configuration and a second, expanded configuration such that outer body 22 and inner body 40 are disposed to engage adjacent vertebral soft tissue and bone surfaces, as will be described, to restore height and provide support in place of removed vertebrae and/or intervertebral tissue.

In operation, implant 10 is disposed in a first orientation, as shown in FIG. 1, such that body 22 and body 40 are disposed in a concentric configuration with longitudinal axis A1 and disposed in a telescopic arrangement for delivery and implantation adjacent a surgical site. Bodies 22, 40 are seated concentrically such that substantially all of inner body 40 is disposed within outer body 22 in a nested configuration. From the first orientation, shaft I is disposed within slot 50 and rotated, in the direction shown by arrow A in FIG. 3, such that teeth 55 of shaft I engage teeth 53 for axial translation of body 40 relative to body 22 and rotation of band 58 relative to bodies 22, 40. As shaft I is rotated in the direction shown by arrow A, teeth 55 engage teeth 53 to drive body 40 in an axial direction, as shown by arrow B in FIG. 4 and cause axial translation of body 40 relative to body 22 to expand implant 20. In one embodiment, shaft I is rotated in a direction shown by arrow AA in FIG. 3 such that teeth 55 engage teeth 53 to drive body 40 in an axial direction, as shown by arrow BB in FIG. 4, and cause axial translation of body 40 relative to body 22 to contract and/or collapse implant 20 from an expanded configuration.

Figure 4:
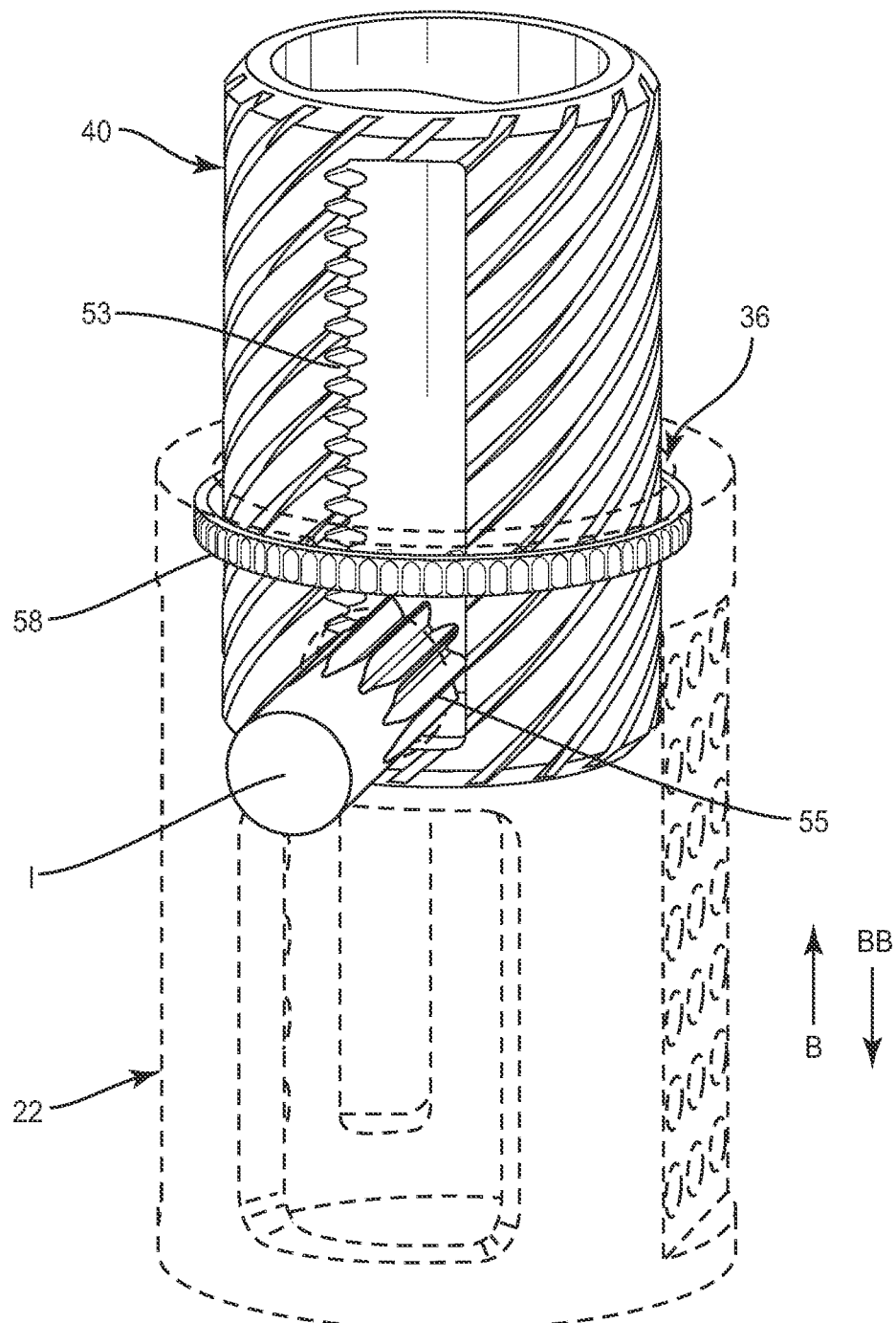
FIG. 4 is a perspective view, in part phantom, of components of the system shown in FIG. 1.
Figure 5:
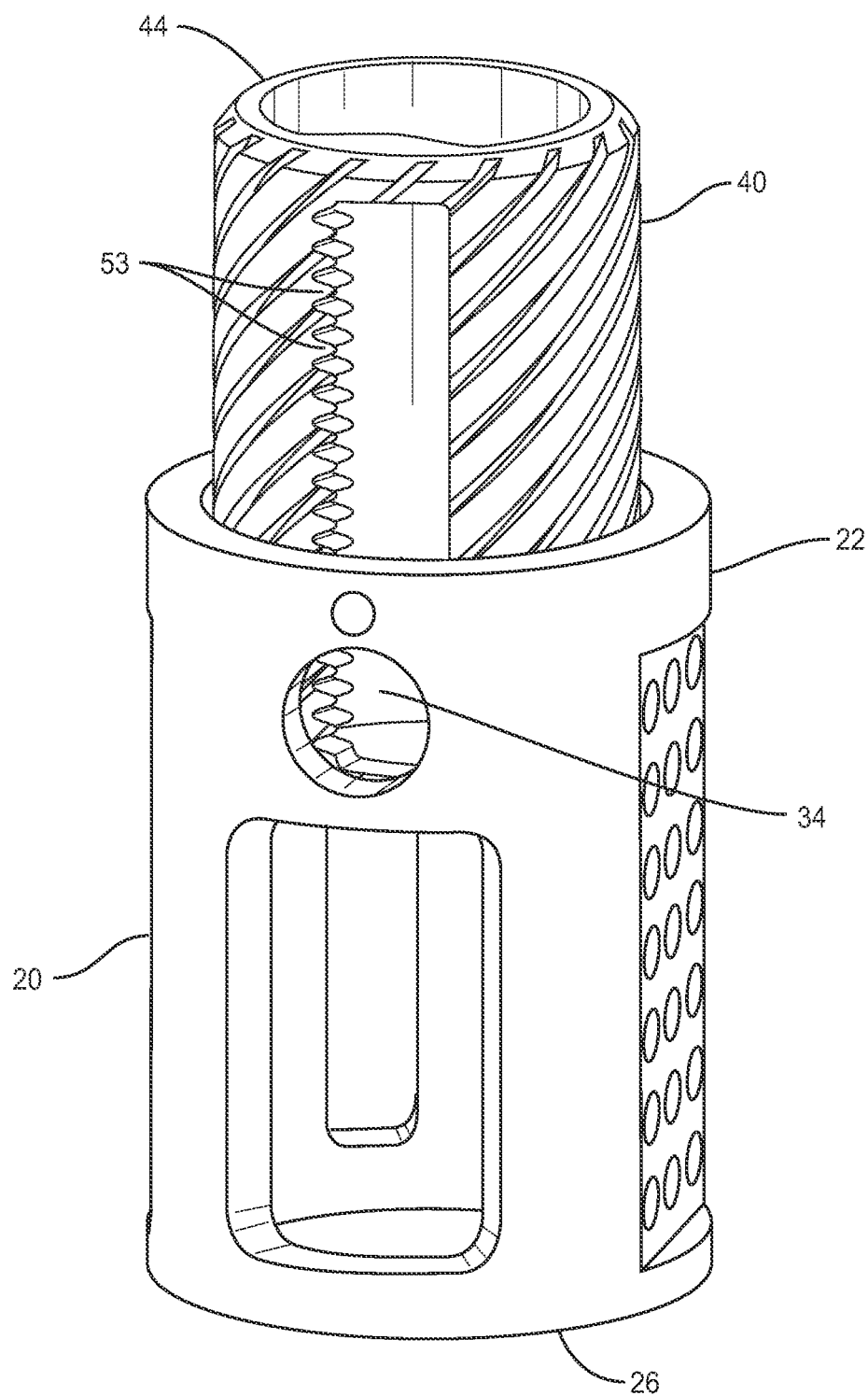
FIG. 5 is a perspective view of components of the system shown in FIG. 1.

As shaft I is rotated in the direction shown by arrow A in FIG. 3, body 40 axially translates, in the direction shown by arrow B in FIG. 4, relative to body 22 such that band 58 slidably rotates within cavity 36 to facilitate expansion of implant 20 via engagement of gears 56, 62. Body 40 axially translates relative to body 22 to a second, expanded orientation, as shown in FIG. 5, such that outer body 22 and inner body 40 are disposed to engage adjacent vertebral soft tissue and bone surfaces, as will be described, to restore height and provide support in place of removed vertebrae and/or intervertebral tissue.

Implant 20 is configured for axial expansion along longitudinal axis A1. In one embodiment, implant 20 may expand in an arcuate configuration along a curvature relative to longitudinal axis A1. It is further contemplated that all or only a portion of implant 20 may be arcuately expanded, such as one or all of bodies 22, 40 may include a curvature relative to longitudinal axis A1.

In one embodiment, implant 20 is expanded to the second orientation at a selected amount of spacing and/or distraction between vertebrae such that end 26 engages a first vertebral surface and end 44 engages a second vertebral surface to restore vertebral spacing and provide distraction and/or restore mechanical support function. In one embodiment, implant 20 is expanded, as discussed herein, progressively and/or gradually to provide an implant configured to adapt to the growth of a patient including the vertebrae. It is envisioned that the height of implant 20 may also be decreased over a period of time and/or several procedures to adapt to various conditions of a patient.

In one embodiment, implant 10 is configured for continuous expansion, which includes incremental expansion due to the configuration and dimension, and resulting engagement of gears 53, 55 and/or gears 56, 62. It is envisioned that incremental expansion may include discrete increments of a particular linear dimension. It is further envisioned that the linear dimension may include a range of approximately 0.1-1.0 mm.

Figure 6:
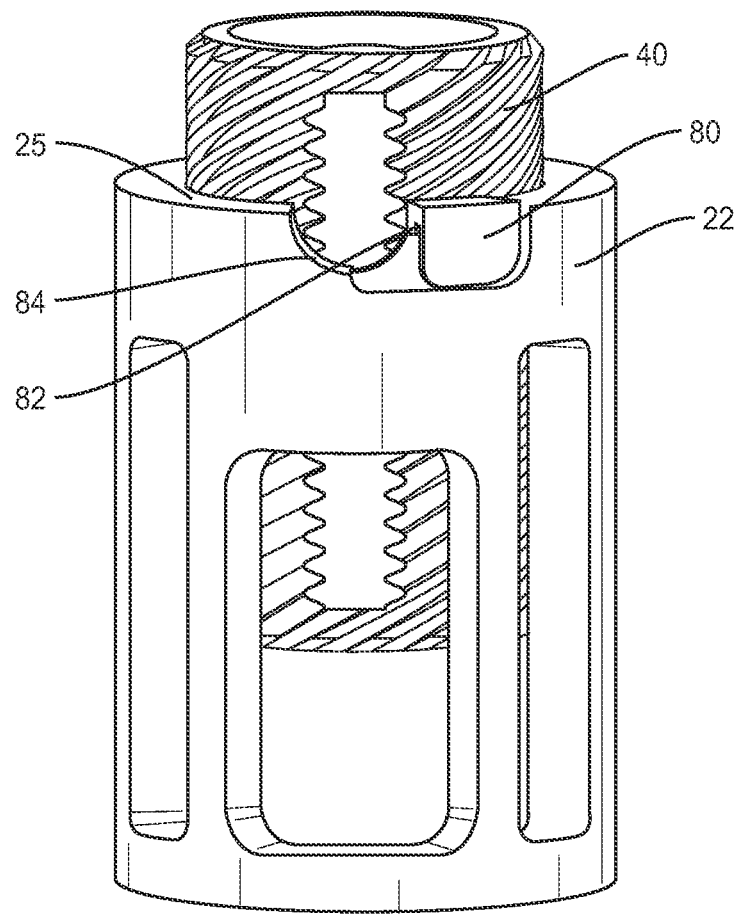
FIG. 6 is a perspective view of components of one embodiment of a surgical system in accordance with the principles of the present disclosure.
Figure 7:
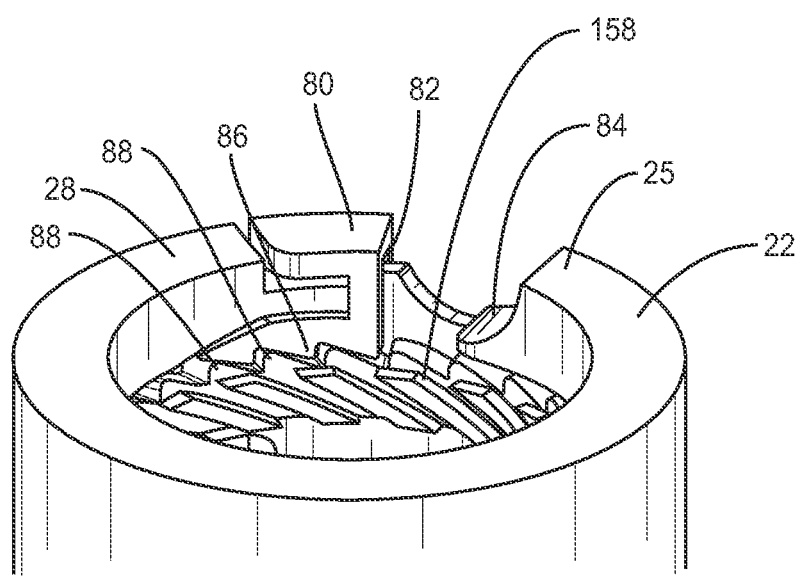
FIG. 7 is an enlarged, break away view of the components of the system shown in FIG. 6.

In one embodiment, as shown in FIGS. 6 and 7, system 10 includes implant 20, similar to that described above with regard to FIGS. 1-5, which includes a sliding lock 80 that is selectively engageable with a band 158, similar to band 58 described herein, to prevent axial translation of body 40 relative to body 22 and rotation of band 158 relative to bodies 22, 40. End face 25 defines a step 82 configured for disposal of lock 80 in a non-locking orientation and a step 84 having a concave configuration and extending a greater depth into end face 25. Step 84 is configured for disposal of lock 80 in a locking orientation.

Lock 80 has an arcuate configuration for slidable disposal with tubular wall 28 such that lock 80 is slidable between the non-locking orientation and the locking orientation. Lock 80 includes a plurality of teeth 86 configured to engage and mate with teeth 88 of band 158. In the non-locking orientation, lock 80 is disposed with step 82 such that teeth 86 are spaced apart from and disposed out of engagement with teeth 88. As such, band 158 is free to rotate relative to bodies 22, 40 and body 40 is free to axially translate relative to body 22, as described herein. Lock 80 is rotatable, via free hand manipulation and/or an instrument, about the circumference and/or perimeter of end face 25 to the locking orientation. Lock 80 is caused to translate axially relative to wall 28 and extend into end face 25 a greater depth for disposal with step 84 to the locking orientation. Teeth 86 are engaged with teeth 88 in a mated orientation such that rotation of band 158 relative to bodies 22, 40 is prevented. As such, body 40 is prevented from axially translating relative to body 22 to fix implant 20 in a selected expanded and/or contracted orientation, including those described herein. It is envisioned that lock 80 and/or band 158 may include one or a plurality of teeth.

Figure 8:
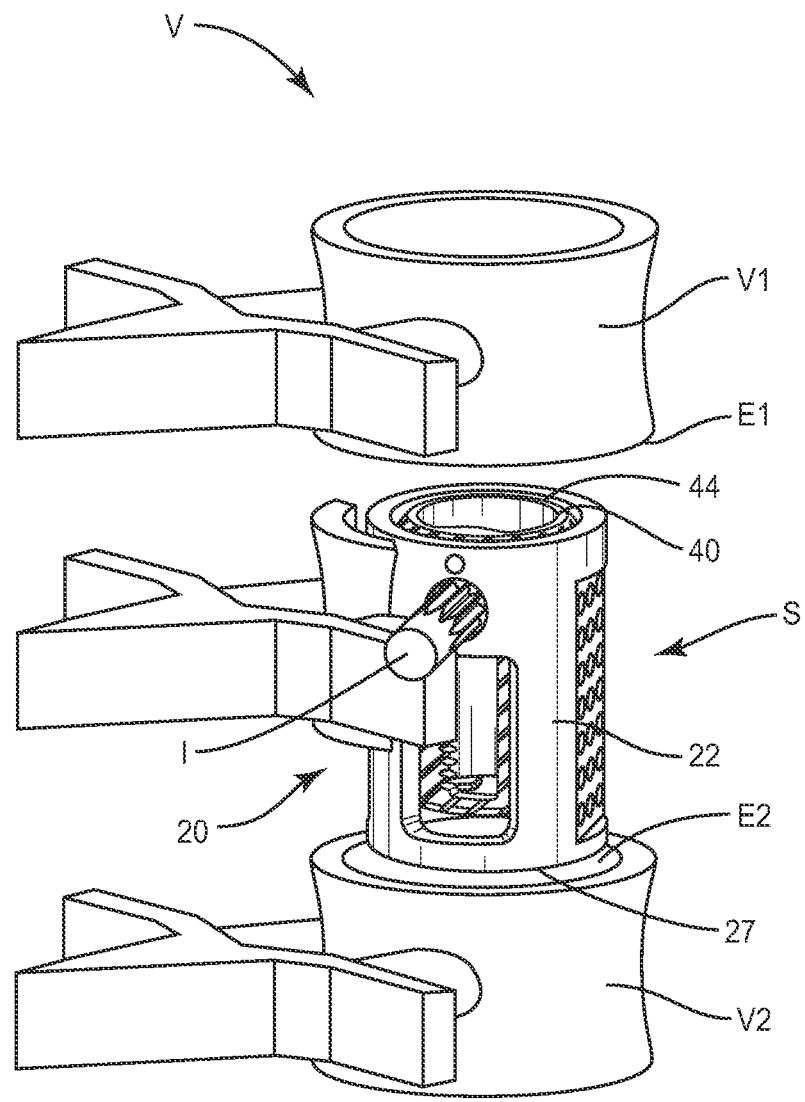
FIG. 8 is a perspective view of components of one embodiment of a surgical system in accordance with the principles of the present disclosure disposed with vertebrae.
Figure 9:
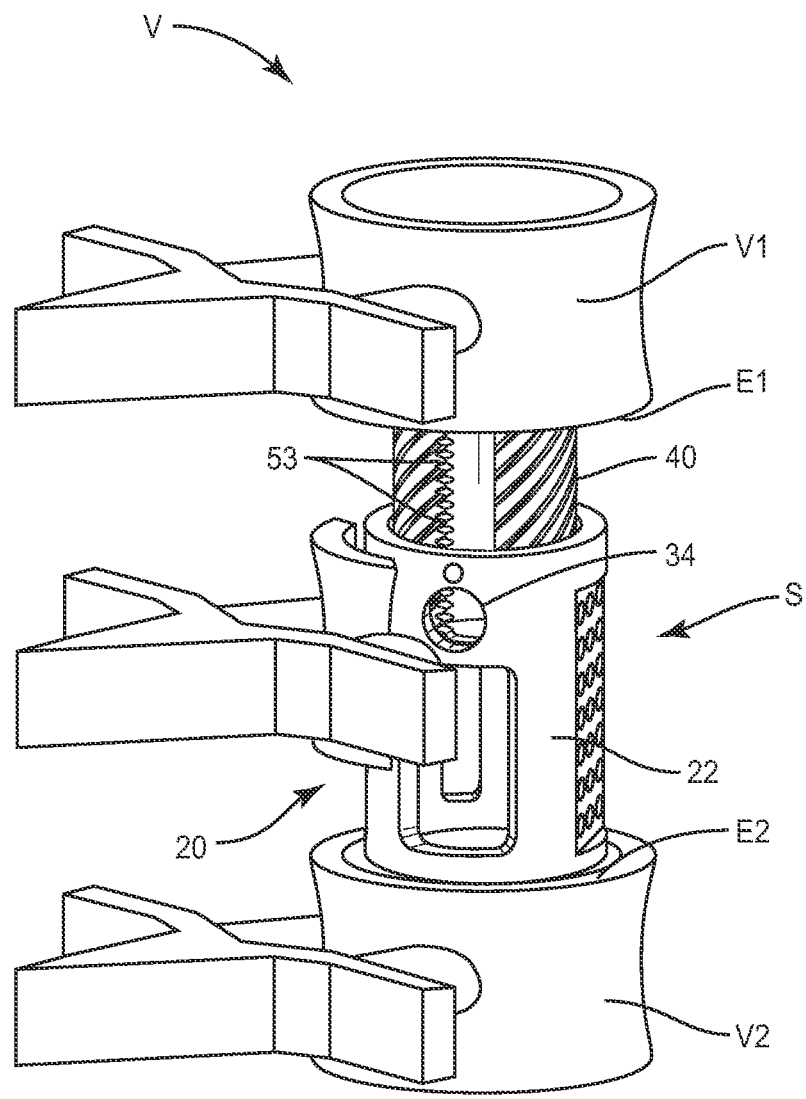
FIG. 9 is a perspective view of components of the system and vertebrae shown in FIG. 8.

Referring to FIGS. 8 and 9, in assembly, operation and use, system 10 including implant 20, similar to that described with regard to FIGS. 1-5, is employed with a surgical procedure, such as, for example, a lumbar corpectomy for treatment of a spine of a patient including vertebrae V. System 10 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners for securement of implant 20.

System 10 is employed with a lumbar corpectomy including surgical arthrodesis, such as, for example, fusion to immobilize a joint for treatment of an applicable condition or injury of an affected section of a spinal column and adjacent areas within a body. For example, vertebrae V includes a first vertebrae V1 and a second vertebrae V2. A diseased and/or damaged vertebrae and intervertebral discs are disposed between the vertebrae V1 and V2. It is contemplated that system 10 is configured for insertion with a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. It is envisioned that system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, corpectomy is performed for treating the spine disorder. The diseased and/or damaged portion of vertebrae V, and diseased and/or damaged intervertebral discs are removed to create a vertebral space S.

A preparation instrument (not shown) is employed to remove disc tissue, fluids, adjacent tissues and/or bone, and scrape and/or remove tissue from endplate surfaces E1 of vertebrae V1 and/or endplate surface E2 of vertebrae V2. Implant 20 is provided with at least one agent, similar to those described herein and as described above, to promote new bone growth and fusion to treat the affected section of vertebrae V.

Implant 10 is disposed in a first orientation, as shown in FIG. 8 and described above with regard to FIGS. 1-5, such that body 22 and body 40 are disposed in a concentric configuration with longitudinal axis A1 and disposed in a telescopic arrangement for delivery and implantation adjacent vertebral space S. Bodies 22, 40 are seated concentrically such that substantially all of inner body 40 is disposed within outer body 22 in a nested configuration. Lock 80, described above with regard to FIGS. 6 and 7, is disposed in a locking orientation such that rotation of a band, similar to those described herein, relative to bodies 22, 40, is prevented and body 40 is prevented from axially translating relative to body 22, as described.

Implant 20 is delivered to the surgical site adjacent vertebrae V with a delivery instrument (not shown) including a driver via the protected passageway for the arthrodesis treatment. The driver delivers implant 20 into the prepared vertebral space S, between vertebrae V1 and vertebrae V2, according to the requirements of a particular surgical application. Implant 20 is manipulated such that end face 27 engages endplate surface E2. A gripping surface of end face 27 penetrates and fixes with endplate surface E2. Implant 20 is positioned in the first orientation with endplate surface E2.

Lock 80 is rotated about the circumference and/or perimeter of end face 25 to the non-locking orientation such that lock 80 translates relative to wall 28 and teeth 86 are spaced apart from teeth 88. As such, the band is free to rotate relative to bodies 22, 40 and body 40 is free to axially translate relative to body 22, as described herein. From the first orientation, shaft I is disposed within slot 50 and rotated, in the direction shown by arrow A in FIG. 3, such that teeth 55 of shaft I engage teeth 53 for axial translation of body 40 relative to body 22. Body 40 axially translates, in the direction shown by arrow B in FIG. 4, relative to body 22 such that the band slidably rotates within cavity 36 to facilitate expansion of implant 20 via engagement of gears 56, 62. Body 40 axially translates relative to body 22 to a second, expanded orientation, as shown in FIG. 9. As such, implant 20 expands within vertebral space S and end 44 engages endplate surface E1. A gripping surface of end 44 penetrates and fixes with endplate surface E1.

Implant 20 engages and spaces apart opposing endplate surfaces E1, E2 and is secured within vertebral space S to stabilize and immobilize portions of vertebrae V in connection with bone growth for fusion and fixation of vertebrae V1, V2. Fixation of implant 20 with endplate surfaces E1, E2 may be facilitated by the resistance provided by the joint space and/or engagement with endplate surfaces E1, E2. Lock 80 is rotated to the locking orientation such that teeth 86 are engaged with teeth 88 in a mated orientation such that rotation of the band relative to bodies 22, 40 is prevented. As such, body 40 is prevented from axially translating relative to body 22 to fix implant 20 in a selected expanded and/or contracted orientation, including those described herein.

It is contemplated that implant 20 may engage only one endplate. It is further contemplated that an agent(s), as described herein, may be applied to areas of the surgical site to promote bone growth. Components of system 10 including implant 20 can be delivered or implanted as a pre-assembled device or can be assembled in situ. Components of system 10 including implant 20 may be completely or partially revised, removed or replaced in situ. It is envisioned that one or all of the components of system 10 can be delivered to the surgical site via mechanical manipulation and/or a free hand technique.

In one embodiment, implant 20 may include fastening elements, which may include locking structure, configured for fixation with vertebrae V1, V2 to secure joint surfaces and provide complementary stabilization and immobilization to a vertebral region. It is envisioned that locking structure may include fastening elements such as, for example, rods, plates, clips, hooks, adhesives and/or flanges. It is further envisioned that system 10 can be used with screws to enhance fixation. It is contemplated that system 10 and any screws and attachments may be coated with an agent, similar to those described herein, for enhanced bony fixation to a treated area. The components of system 10 can be made of radiolucent materials such as polymers. Radiomarkers may be included for identification under x-ray, fluoroscopy, CT or other imaging techniques.

In one embodiment, system 10 includes a plurality of implants 20. It is contemplated that employing a plurality of implants 20 can optimize the amount vertebral space S can be spaced apart such that the joint spacing dimension can be preselected. The plurality of implants 20 can be oriented in a side by side engagement, spaced apart and/or staggered.

It is envisioned that the use of microsurgical and image guided technologies may be employed to access, view and repair spinal deterioration or damage, with the aid of system 10. Upon completion of the procedure, the non-implanted components, surgical instruments and assemblies of system 10 are removed and the incision is closed.

Figure 10:
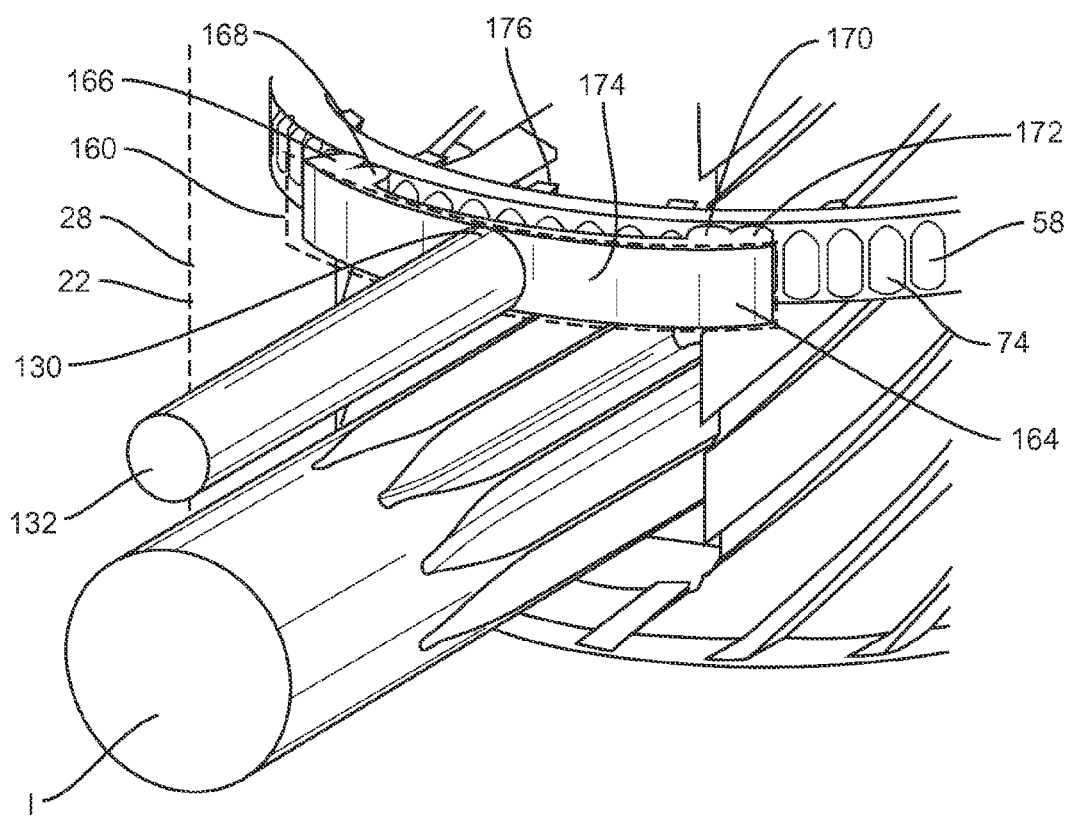
FIG. 10 is an enlarged, break away view, in part phantom, of components of one embodiment of a surgical system in accordance with the principles of the present disclosure.

In one embodiment, as shown in FIG. 10, system 10, similar to the system and methods described with regard to FIGS. 1-5 and 8-9, includes implant 20 having a spring lock 164 engageable with band 58, described above, to prevent axial translation of body 40 relative to body 22 and rotation of band 58 relative to bodies 22, 40. Wall 28 defines a cavity 160 configured for disposal of lock 164.

Lock 164 has a leaf spring configuration and includes teeth 166 disposed at a first end 168 of lock 164 and teeth 170 disposed at a second end 172 of lock 164. Teeth 166 are spaced apart from teeth 168 along an arcuate portion 174 of lock 164, and teeth 166, 168 are configured to engage and mate with teeth 74 of band 58. Wall 28 defines an opening 130 configured to receive a tool, such as, for example, a spring depressor 132. Depressor 132 is slidable in transverse translation through opening 130 to engage arcuate portion 174 for disposal of lock 164 between a locking orientation and a non-locking orientation.

In a locking orientation, arcuate portion 174 is spring biased such that teeth 166, 168 are disposed in mated engagement with teeth 74. As such, band 58 is prevented from rotating relative to bodies 22, 40 and body 40 is prevented from axially translating relative to body 22. Prior to rotation of shaft I and actuation of bodies 22, 40, depressor 132 is translated through opening 130 to engage arcuate portion 174 to overcome the spring bias of lock 164. As arcuate portion 174 is depressed, ends 168, 172 are forcedly outwardly away and pivot from wall 28 to space teeth 166, 168 apart from and out of engagement with teeth 74. Wall 28 includes a portion 176 that prevents arcuate portion 174 from engaging teeth 74 as arcuate portion 174 is being manipulated. As such, band 58 is free to rotate relative to bodies 22, 40 and body 40 is free to axially translate relative to body 22, as described herein. Upon selected expansion and/or contraction of implant 20, depressor 132 is removed from opening 130 and arcuate portion 174 is biased to the locking orientation such that teeth 166, 168 are disposed in mated engagement with teeth 74. As such, band 58 is prevented from rotating relative to bodies 22, 40 and body 40 is prevented from axially translating relative to body 22 to fix implant 20 in a selected expanded and/or contracted orientation, including those described herein.

Figure 11:
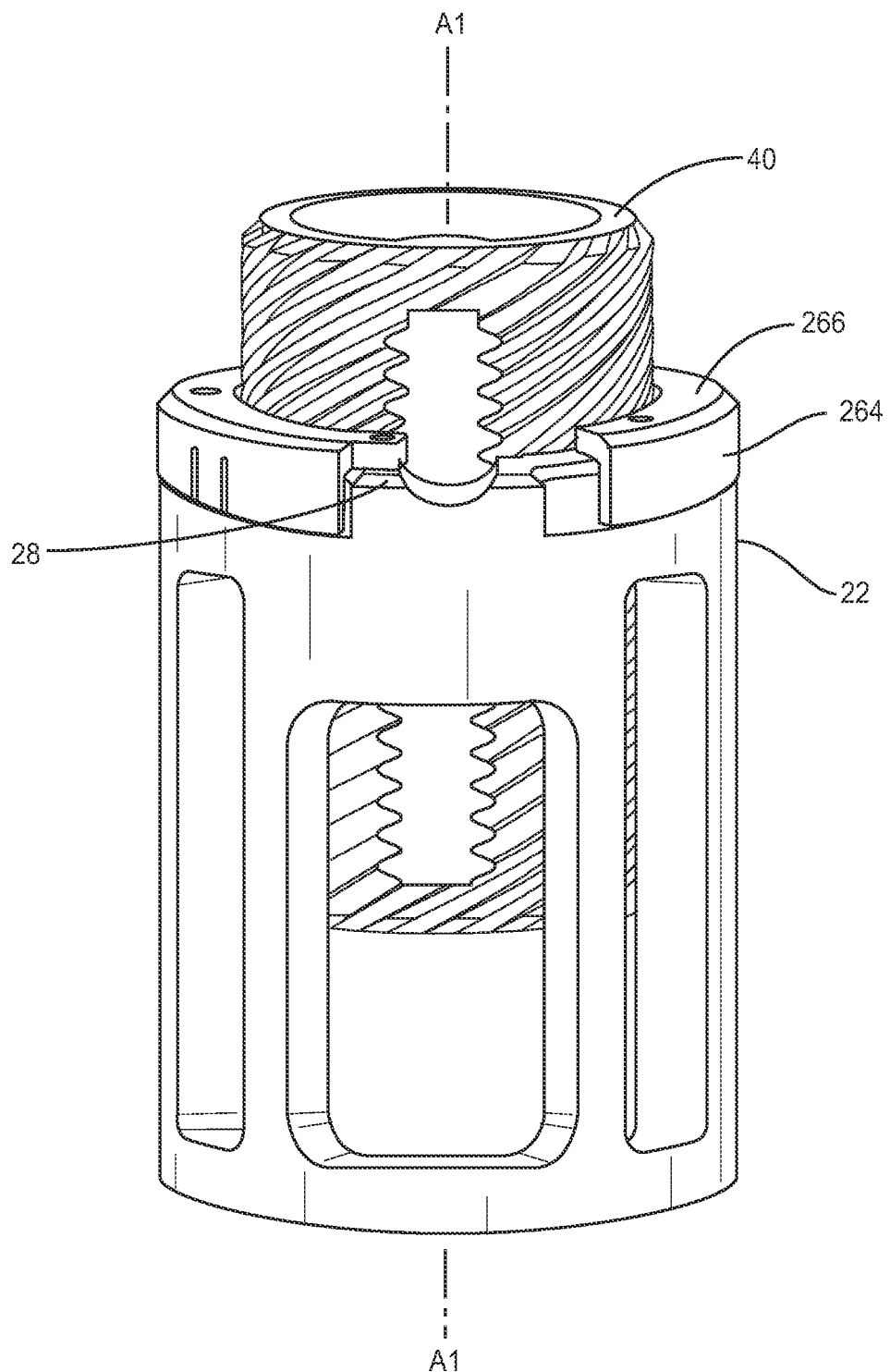
FIG. 11 is a perspective view of components of one embodiment of a surgical system in accordance with the principles of the present disclosure.
Figure 12:
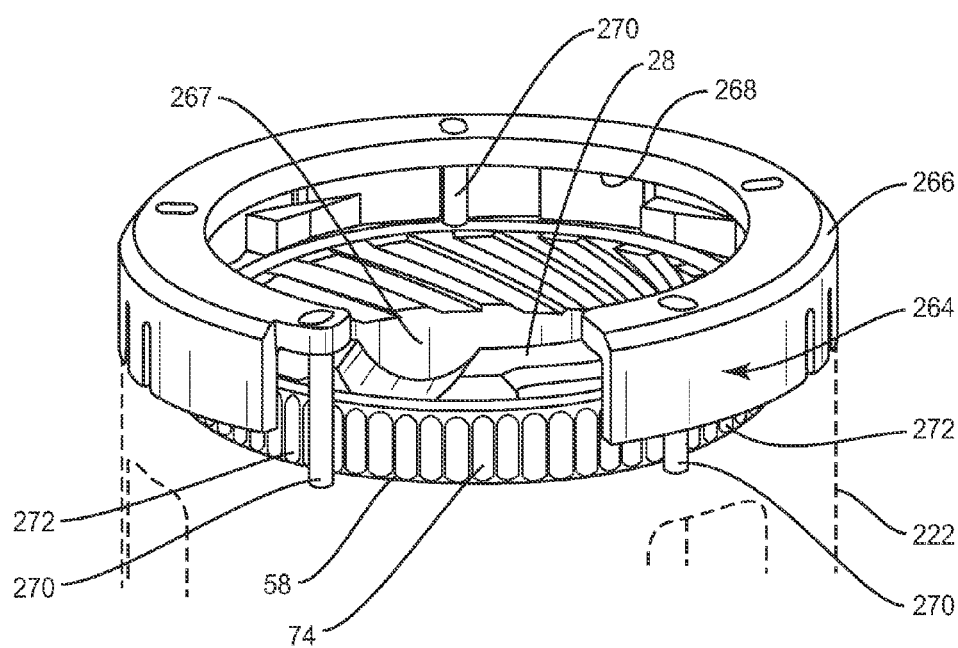
FIG. 12 is an enlarged, break away view of components of the system shown in FIG. 11.

In one embodiment, as shown in FIGS. 11 and 12, system 10, similar to the system and methods described above, includes implant 20 having a pin lock 264 engageable with band 58, described above, to prevent axial translation of body 40 relative to body 22 and rotation of band 58 relative to bodies 22, 40. Lock 264 includes a circumferential collar 266 mounted with and disposed about end 24 of wall 28. Collar 266 includes an open and non-continuous portion 267.

Collar 266 includes an inner surface 268 having a plurality of pins 270 extending axially therefrom. Pins 270 are spaced apart and disposed in a circumferential configuration about surface 268. Pins 270 are configured to engage and mate with teeth 74 of band 58. Collar 266 is rotatable relative to wall 28 and band 58 such that pins 270 are rotatable and translatable along an arcuate trajectory toward and away from axis A1 to engage and disengage teeth 74 for disposal of lock 264 between a locking orientation and a non-locking orientation.

Wall 28 includes slots 272 configured for slidable disposal of pins 270. Slots 272 have an arcuate configuration and define the arcuate trajectory and path of pins 270 as they are rotated. It is contemplated that collar 266 may include one or a plurality of pins 270. It is contemplated that the number of pins 270 can be adjusted depending on an axial load applied to implant 20, for example, approximately 4 kiloNewtons (kN) for upper thoracic applications and/or approximately 6 kN for lower thoracic/lumbar applications.

In a locking orientation, lock 264 mates with end 24 and pins 270 nest between teeth 74. As such, band 58 is prevented from rotating relative to bodies 22, 40 and body 40 is prevented from axially translating relative to body 22. Prior to rotation of shaft I and actuation of bodies 22, 40, collar 266 is rotated, for example, in a clockwise direction, such that pins 270 rotate and translate along the arcuate trajectory of slots 272, described above. Slots 272 drive pins 270 outward from axis A1 to disengage and space pins 270 apart from teeth 74. As such, band 58 is free to rotate relative to bodies 22, 40 and body 40 is free to axially translate relative to body 22, as described herein.

Upon selected expansion and/or contraction of implant 20, collar 266 is rotated, for example, in a counter clockwise direction, to the locking orientation such that pins 270 rotate and slots 272 drive pins 270 inwardly for fixation with teeth 74, as described above. As such, band 58 is prevented from rotating relative to bodies 22, 40 and body 40 is prevented from axially translating relative to body 22 to fix implant 20 in a selected expanded and/or contracted orientation, including those described herein.

Figure 13:
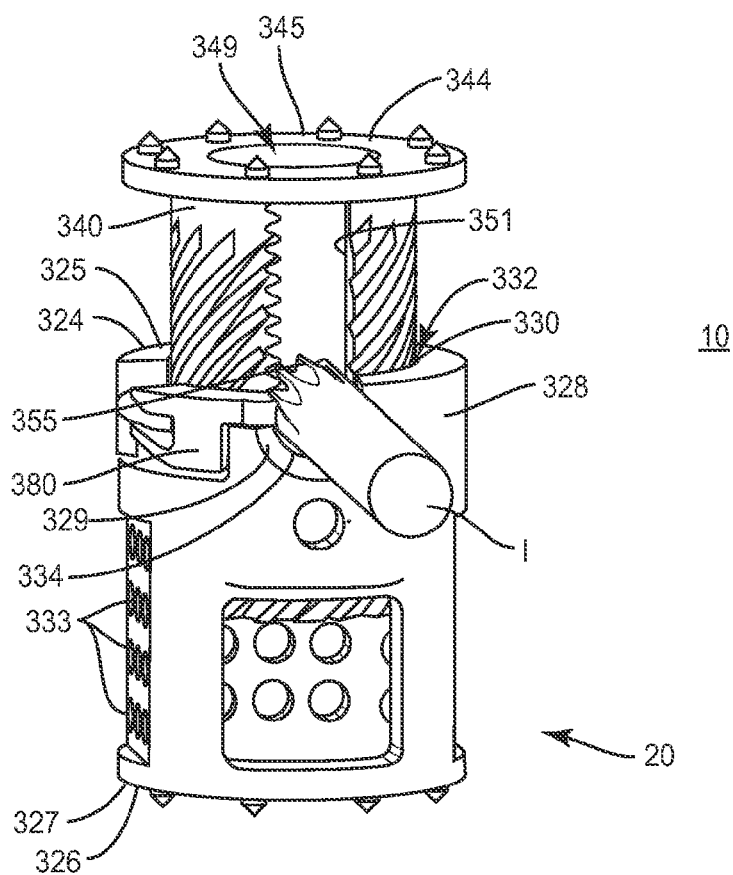
FIG. 13 is a perspective view of components of one embodiment of a surgical system in accordance with the principles of the present disclosure.
Figure 14:
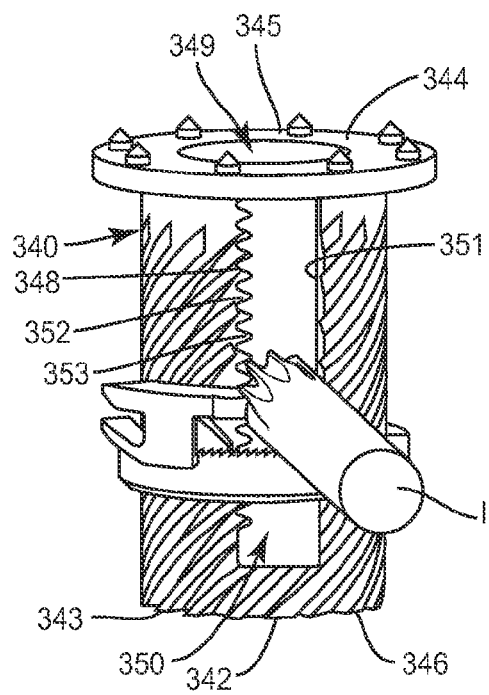
FIG. 14 is a cutaway perspective view of components of the system shown in FIG. 13.

In one embodiment, as shown in FIGS. 13 and 14, system 10, similar to the system and methods described above with regard to FIGS. 1-9, includes implant 20 having an outer body 322, similar to body 22 described above. Body 322 extends between a first end 324 and a second end 326. End 324 defines an end face 325 including a substantially planar surface configured to engage vertebral tissue. End 326 defines an end face 327 including a substantially planar surface configured to engage vertebral tissue. End face 327 includes a plurality of spikes extending therefrom configured for fixation with vertebral tissue.

Body 322 includes a wall 328 having an inner surface 330 that defines an axial cavity 332 extending between ends 324, 326. Wall 328 defines openings 333 configured to receive an agent, similar to openings 33 described above.

Wall 328 includes an inwardly oriented surface 329 that defines a lateral, U-shaped cavity 334. Cavity 334 is configured for disposal of an instrument utilized to facilitate expansion of body 322 and an inner body 340, similar to body 40 described above. Cavity 334 is oriented for disposal of pinion gear shaft I, described above, configured for engagement with gear teeth of body 340. Surface 330 defines a circumferential cavity (not shown), similar to cavity 36 described above, disposed adjacent end 324, which is configured for disposal of a band 358, similar to band 58 described above. Band 358 is slidably movable within the circumferential cavity for rotation relative to body 340. Disposal of shaft I within cavity 334 positions shaft I above band 358. This configuration of shaft I above band 358 facilitates expansion of bodies 322, 340 to provide an increased expansion height of bodies 322, 340.

Body 340 is oriented for disposal within axial cavity 332. Body 340 extends between a first end 342 and a second end 344. End 342 defines an end face 343 including a substantially planar surface that is configured to engage vertebral tissue. End 344 defines an end face 345 including a substantially planar surface that is configured to engage vertebral tissue. End face 345 includes a plurality of spikes extending therefrom configured for fixation with vertebral tissue.

Body 340 includes a wall 346 that defines an axial cavity 349, similar to cavity 49 described above, extending between ends 342, 344. Body 340 is configured for disposal with cavity 332 such that walls 328, 346 are concentric. Wall 346 includes a plurality of inwardly oriented surfaces, which include an axial surface 348 and side surfaces 351, similar to surfaces 48, 51 described above. Surfaces 348, 351 are each disposed in a relatively perpendicular orientation to each other to define an axial slot 350, similar to slot 50 described above.

Surface 348 includes a gear rack 352, similar to rack 52 described above, having a plurality of teeth 353 that are disposed therealong. Shaft I is disposed within cavity 334 and slot 350 for relative axial translation of body 340 and rotation such that circumferentially disposed gear teeth 355 of shaft I engage teeth 353. As shaft I is rotated, teeth 355 engage teeth 353 to drive body 340 in an axial direction and cause axial translation of body 340 relative to body 322 to expand implant 20, similar to the configuration of components of system 20, operation and methods described above. This configuration of shaft I being disposed with cavity 334 above band 358, as shown in FIG. 14, facilitates expansion of bodies 322, 340 to provide an increased expansion height of bodies 322, 340. Implant 20 includes a sliding lock 380, similar to the configuration of lock 80, operation and methods described above, to prevent axial translation of body 340 relative to body 322.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   a first member defining a longitudinal axis and including a wall that defines an axial cavity and at least one lateral opening configured for disposal of an instrument;
   a second member configured for disposal with the axial cavity and including a wall having an axial surface disposed along a thickness thereof, the axial surface defining at least a portion of an axial opening and including a plurality of gear teeth disposed therealong; and
   a third member comprising a circumferential ring configuration, the third member being rotatable relative to the inner surface and engageable with the second member,
   wherein the instrument is directly engageable with the teeth to axially translate the second member relative to the first member, and the first member comprises a lock selectively engageable with the third member to prevent the axial translation, the lock being prevented from translating axially relative to the first member.

2. A spinal implant as recited in claim 1, wherein the wall of the first member includes an inner surface that defines a circumferential cavity configured for disposal of the third member.

3. A spinal implant as recited in claim 1, wherein the third member includes an inner surface that defines a helical gear engageable with a helical gear of an outer surface of the second member.

4. A spinal implant as recited in claim 1, wherein the lock is rotatable relative to the first member.

5. A spinal implant as recited in claim 1, wherein the lock includes at least one tooth engageable with at least one tooth of the third member.

6. A spinal implant as recited in claim 1, wherein the lock includes a leaf spring engageable with the third member.

7. A spinal implant as recited in claim 6, wherein the leaf spring includes gear teeth biased for engagement with gear teeth of the third member to prevent the axial translation, the leaf spring being engageable to pivot the gear teeth thereof out of engagement with the gear teeth of the third member.

8. A spinal implant as recited in claim 1, wherein the lock includes a collar having at least one axial pin, the collar being rotatable relative to the first member to move the pin into and out of engagement with the third member.

9. A spinal implant as recited in claim 1, further including the instrument, wherein the instrument includes a pinion gear shaft engageable with the teeth.

10. A spinal implant as recited in claim 1, further including the instrument, wherein the instrument is disposed in the lateral opening and rotatable relative to the first member for engagement with the teeth.

11. A spinal implant as recited in claim 1, wherein the teeth are disposed in a linear, serial configuration.

12. A spinal implant as recited in claim 1, wherein the wall of the second member includes a plurality of even surfaces and the axial surface to define the axial opening.

13. A spinal implant as recited in claim 1, wherein the members axially translate between a contracted configuration and an expanded configuration.

14. A spinal implant as recited in claim 1, wherein the third member has a fixed diameter.

15. A spinal implant as recited in claim 1, wherein the axial surface comprises a helical gear and an inner surface of the third member comprises a plurality of teeth that are engageable with the helical gear.

16. A spinal implant as recited in claim 1, wherein an outer surface of the third member comprises a spur gear having a plurality of axially oriented and spaced apart teeth and the lock comprises spaced apart teeth that are configured to engage the spur gear to prevent the axial translation.

17. A spinal implant as recited in claim 1, wherein an outer surface of the third member comprises a spur gear having a plurality of axially oriented and spaced apart teeth and the lock comprises a collar having an axial pin configured for disposal between the teeth to prevent the axial translation.

18. A spinal implant as recited in claim 2, wherein the first member is free of any openings that extend through an outer surface of the first member and are in communication with the circumferential cavity.

19. A spinal implant comprising:
a first member defining a longitudinal axis and including a wall that defines an axial cavity and at least one lateral opening configured for disposal of an instrument, the wall including an inner surface that defines a circumferential cavity;
a second member configured for disposal with the axial cavity and including a wall having an axial surface disposed along a thickness thereof, the axial surface defining at least a portion of an axial opening and including a plurality of gear teeth disposed therealong; and
a third member disposed in the circumferential cavity,
wherein the instrument is directly engageable with the teeth to axially translate the second member relative to the first member,
wherein the third member is rotatable relative to the inner surface and engageable with the second member, and
wherein the first member includes a lock selectively engageable with the third member to prevent the axial translation, the lock including a leaf spring engageable with the third member.

20. A spinal implant comprising:
a first member defining a longitudinal axis and including a wall that defines an axial cavity and at least one lateral opening configured for disposal of an instrument, the wall including an inner surface that defines a circumferential cavity;
a second member configured for disposal with the axial cavity and including a wall having an axial surface disposed along a thickness thereof, the axial surface defining at least a portion of an axial opening and including a plurality of gear teeth disposed therealong; and
a third member disposed in the circumferential cavity,
wherein the instrument is directly engageable with the teeth to axially translate the second member relative to the first member,
wherein the third member is rotatable relative to the inner surface and engageable with the second member, and
wherein the first member includes a lock selectively engageable with the third member to prevent the axial translation, the lock including a collar having at least one axial pin, the collar being rotatable relative to the first member to move the pin into and out of engagement with the third member.

* * * * *